(12) United States Patent
Freda et al.

(10) Patent No.: US 9,482,645 B2
(45) Date of Patent: *Nov. 1, 2016

(54) ULTRASONIC DETECTION METHOD AND ULTRASONIC ANALYSIS METHOD

(71) Applicant: GENERAL ELECTRIC COMPANY, Schenectady, NY (US)

(72) Inventors: Michael Charles Freda, Warren, NJ (US); Francis Alexander Reed, Duanesburg, NY (US)

(73) Assignee: General Electric Company, Schenectady, NY (US)

( * ) Notice: Subject to any disclaimer, the term of this patent is extended or adjusted under 35 U.S.C. 154(b) by 473 days.

This patent is subject to a terminal disclaimer.

(21) Appl. No.: 13/896,408

(22) Filed: May 17, 2013

(65) Prior Publication Data
US 2014/0338456 A1    Nov. 20, 2014

(51) Int. Cl.
*G01N 29/11* (2006.01)
*G01N 29/26* (2006.01)

(52) U.S. Cl.
CPC .............. *G01N 29/262* (2013.01); *G01N 29/11* (2013.01); *G01N 2291/2693* (2013.01)

(58) Field of Classification Search
CPC ...... G01N 29/04; G01N 29/26; G01N 29/34; G01N 29/44; G01N 29/07; G01N 29/24; G01N 29/36; G01N 27/82; G01N 29/27
USPC ......... 73/641, 642, 660, 622, 621, 626, 625, 73/602, 628, 632
See application file for complete search history.

(56) References Cited

U.S. PATENT DOCUMENTS 4,137,779 A * 2/1979 Wustenberg et al. .......... 73/627
4,497,210 A    2/1985 Uchida et al.

(Continued)

FOREIGN PATENT DOCUMENTS

CN    1169463 A    1/1998
EP    263475 A3    10/1987

(Continued)

OTHER PUBLICATIONS

Moles, Michael. NDT Solution, Construction Weld Testing Procedures Using Ultrasonic Phased Arrays, Copyright 2012, The American Society for Nondestructive Testing. http://www.asnt.org/publications/Materialseval/solution/jan05solution/jan05sol.htm.

(Continued)

*Primary Examiner* — J M Saint Surin
(74) *Attorney, Agent, or Firm* — McNees Wallace & Nurick LLC

(57) ABSTRACT

Ultrasonic detection methods are disclosed. The method includes providing an ultrasonic detection system having a transmitting phased array device and a receiving phased array device. A phased array wave is transmitted through a revolutionary body from the transmitting phased array device to the receiving phased array device, thereby obtaining ultrasonic detection information about the revolutionary body. In another embodiment, the method includes positioning the transmitting phased array device and the receiving phased array device on a periphery of a turbine rotor, transmitting a phased array wave into the turbine rotor, the phased array wave not reflecting off of a reflecting feature, adjusting the positioning of the transmitting phased array devices on the periphery of the turbine rotor, and transmitting the phased array wave into the turbine rotor, the phased array wave reflecting off of a reflecting feature. The reflected phased array wave is received by the receiving phased array device.

20 Claims, 1 Drawing Sheet

(56) References Cited

U.S. PATENT DOCUMENTS

| | | | |
|---|---|---|---|
| 4,523,468 A * | 6/1985 | Derkacs | G01N 29/07 73/598 |
| 4,552,021 A | 11/1985 | Miwa et al. | |
| 4,570,487 A | 2/1986 | Gruber | |
| 4,760,737 A | 8/1988 | Kupperman | |
| 4,821,575 A | 4/1989 | Fujikake et al. | |
| 5,445,029 A | 8/1995 | Falsetti | |
| 5,618,994 A * | 4/1997 | Falsetti | 73/602 |
| 5,714,689 A | 2/1998 | Latimer et al. | |
| 5,770,800 A | 6/1998 | Jenkins et al. | |
| 5,963,882 A | 10/1999 | Viertl et al. | |
| 6,725,722 B1 | 4/2004 | Murphy et al. | |
| 7,017,414 B2 | 3/2006 | Falsetti et al. | |
| 7,245,789 B2 | 7/2007 | Bates et al. | |
| 7,255,007 B2 | 8/2007 | Messer et al. | |
| 7,302,851 B2 | 12/2007 | Czerw et al. | |
| 7,428,842 B2 | 9/2008 | Fair et al. | |
| 8,438,929 B2 * | 5/2013 | Metala | G01M 13/00 73/593 |
| 2002/0088282 A1 * | 7/2002 | Zayicek | G01N 29/069 73/628 |
| 2004/0067000 A1 | 4/2004 | Bates et al. | |
| 2004/0244491 A1 | 12/2004 | Vyas et al. | |
| 2005/0022602 A1 | 2/2005 | Falsetti et al. | |
| 2005/0126291 A1 | 6/2005 | Czerw et al. | |
| 2006/0283250 A1 | 12/2006 | Fair et al. | |
| 2007/0000328 A1 | 1/2007 | Buttram | |
| 2007/0119255 A1 | 5/2007 | Czerw et al. | |
| 2008/0121040 A1 | 5/2008 | MacLauchlan et al. | |
| 2008/0236287 A1 | 10/2008 | Van Agthoven et al. | |
| 2010/0043558 A1 | 2/2010 | Fuller | |
| 2011/0109627 A1 | 5/2011 | Zhang et al. | |
| 2011/0120223 A1 | 5/2011 | MacLauchlan et al. | |
| 2011/0277549 A1 | 11/2011 | Frederick et al. | |
| 2011/0296923 A1 | 12/2011 | Cataldo et al. | |
| 2012/0055255 A1 | 3/2012 | Metala et al. | |
| 2013/0291640 A1 * | 11/2013 | Rasselkorde | G01N 29/043 73/625 |

FOREIGN PATENT DOCUMENTS

| | | |
|---|---|---|
| EP | 263475 B1 | 2/1996 |
| EP | 1918701 A1 | 5/2008 |
| EP | 1927856 A2 | 6/2008 |
| EP | 2073003 A1 | 6/2009 |
| EP | 2765417 A1 | 8/2014 |
| JP | 61080044 A2 | 4/1986 |
| JP | 5288723 A2 | 4/1992 |
| WO | 9807373 A1 | 2/1998 |
| WO | 2004032746 A2 | 4/2004 |
| WO | 2009144717 A2 | 12/2009 |
| WO | 2010097269 A1 | 9/2010 |
| WO | 2012030520 A1 | 3/2012 |
| WO | 2013165817 A1 | 11/2013 |

OTHER PUBLICATIONS

Granillo, Jesse. Back to Basics, Portable Phased Array Applications. Copyright 2012, The American Society for Nondestructive Testing. http://www.asnt.org/publications/materialseval/basics/apr05basics/apr05basics.htm.

GE Inspection Technologies. Phasor XS—Portable Phased Array Ultrasonic Flaw Dectector, Copyright 2007, General Electric Company. http://www.everestvit.com/download/ultrasound/portable-flaw-detectors/phasor%20Series/GEIT-20050EN_phasorxs-brochure.pdf.

GB Combined Search and Examination Report issued in connection with corresponding Application No. GB1408520.3 on Nov. 13, 2014.

* cited by examiner

ULTRASONIC DETECTION METHOD AND ULTRASONIC ANALYSIS METHOD

FIELD OF THE INVENTION

The present invention is directed to non-destructive testing methods. More specifically, the present invention is directed to ultrasonic detection and analysis methods.

BACKGROUND OF THE INVENTION

The inspection of large and complex objects (such as, solid steam turbine rotors) can be very difficult. Such inspection is important for identifying features, such as, asperities, voids, defects, fatigued material, cracks, and/or material variations. In large objects, non-destructive techniques are limited based upon the size of the objects, based upon the complexity of the objects, and/or based upon the materials of the objects. A failure to identify such features can result in extended repair cycles, limiting availability of operation, and/or system failure.

Some commercial inspection systems are available to provide the inspection of large objects. Known ultrasonic techniques use single probe approaches, limiting the volume of material that can be inspected in a single pass. For example, one known technique, pulse echo, is limited to covering a small volume of a cylindrical solid rotor material in a single pass.

To achieve such inspection in a non-destructive manner, ultrasonic systems can be integrated into the object at a substantial expense, can require complex and/or repeated analysis, can require advanced motion control and/or complex probe positioning control, and combinations thereof, resulting in high costs.

An ultrasonic detection method and ultrasonic analysis method that do not suffer from one or more of the above drawbacks would be desirable in the art.

BRIEF DESCRIPTION OF THE INVENTION

In one embodiment, an ultrasonic detection method includes providing an ultrasonic detection system having a transmitting phased array device and a receiving phased array device. A phased array wave or beam is transmitted through a turbine rotor from the transmitting phased array device to the receiving phased array device, thereby obtaining ultrasonic detection information about the turbine rotor.

In another embodiment, an ultrasonic detection method includes providing an ultrasonic detection system having a transmitting phased array device and a receiving phased array device, positioning the transmitting phased array device and the receiving phased array device on a periphery of a turbine rotor, transmitting a phased array wave or beam from the transmitting phased array device into the turbine rotor, the phased array wave or beam not reflecting off of a reflecting feature, adjusting the positioning of the transmitting phased array device and the receiving phased array device on the periphery of the turbine rotor, and transmitting the phased array wave or beam from the transmitting phased array device into the turbine rotor, the phased array wave or beam reflecting off of a reflecting feature. The reflected phased array wave or beam is received by the receiving phased array device.

In another embodiment, an ultrasonic analysis method includes detecting a reflecting feature within a revolutionary body, providing an ultrasonic analysis system having a transmitting phased array device and a receiving phased array device, positioning a plurality of the transmitting phased array devices and receiving phased array devices in a predetermined configuration around the reflecting feature, transmitting phased array waves or beams from the plurality of the transmitting phased array devices into the revolutionary body, reflecting the phased array waves or beams off of the reflecting feature within the revolutionary body, and receiving the phased array waves or beams at the plurality of receiving phased array devices, thereby obtaining ultrasonic information about the reflecting feature.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWINGS

Wherever possible, the same reference numbers will be used throughout the drawings to represent the same parts.

DETAILED DESCRIPTION OF THE INVENTION

Provided is an exemplary ultrasonic detection method. Embodiments of the present disclosure, in comparison to methods not utilizing one or more features disclosed herein, permit non-destructive analysis of features in large solid or substantially solid objects, reduce or eliminate repair and/or inspection cycles, utilize two or more probes in a pitch-catch manner, avoid integration of probes into large bodies, or a combination thereof.

Figure 1:
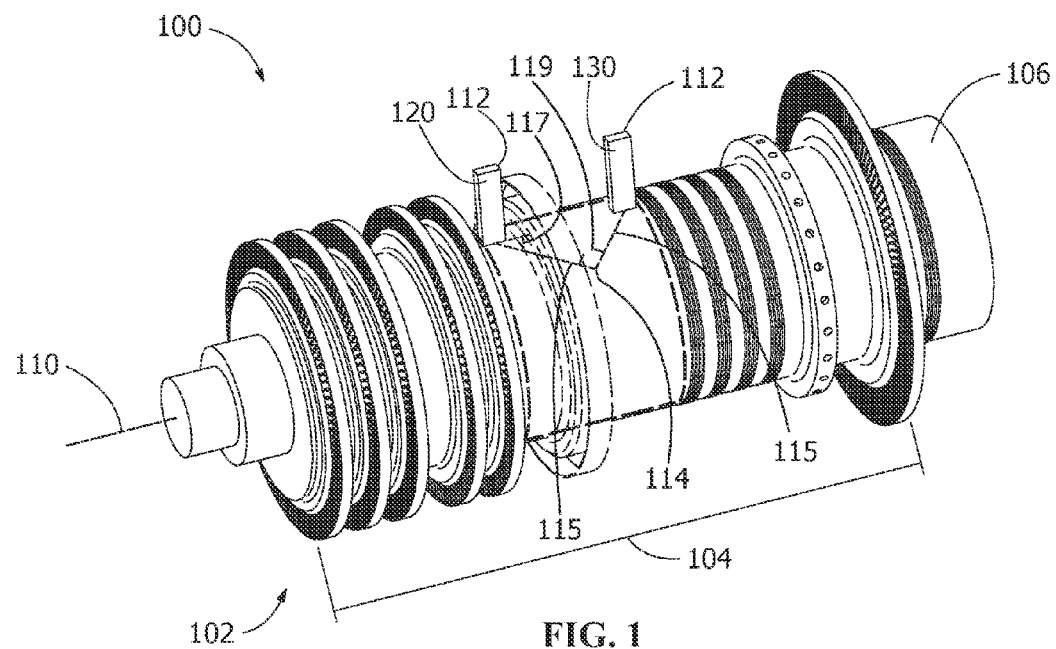
FIG. 1 is a perspective view of an ultrasonic detection system with a reflecting feature at a first position within an object analyzed by an embodiment of an ultrasonic detection method according to the disclosure.
Figure 2:
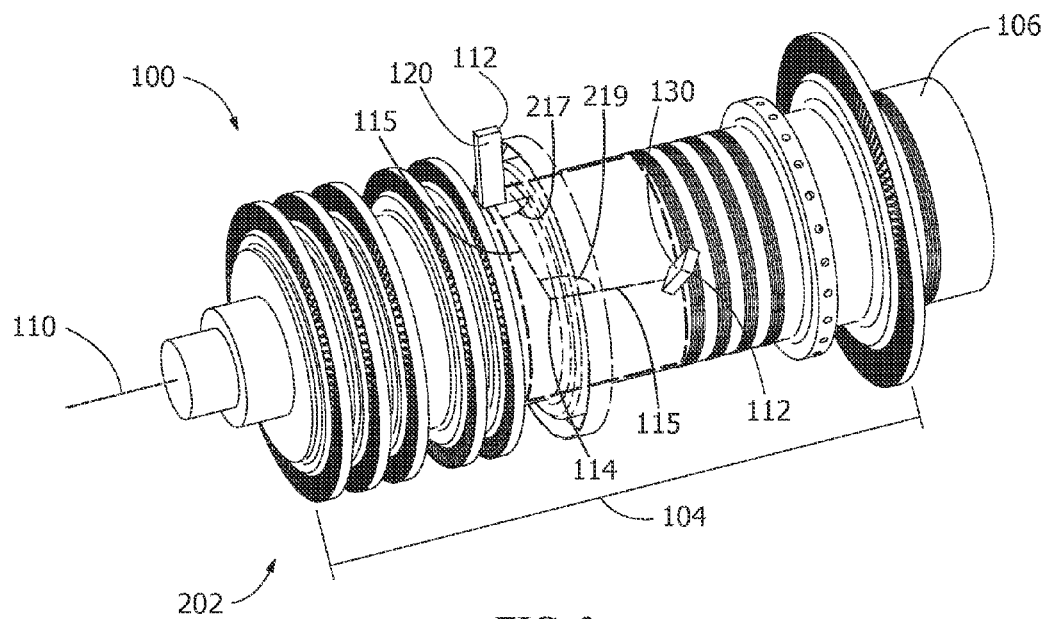
FIG. 2 is a perspective view of an ultrasonic detection system with a reflecting feature at a second position within an object analyzed by an embodiment of an ultrasonic detection method according to the disclosure.

FIGS. 1 and 2 show embodiments of an ultrasonic detection system 100 for performing an ultrasonic detection method. The system 100 includes two or more ultrasonic phased array devices 112 arranged with respect to a revolutionary body 106 to be measured. The revolutionary body 106 is rotatable about a centerline, and is any suitable object including, but not limited to, objects manufactured from a monolithic forging, such as, a turbine rotor, a shaft of a solid steam rotor, a portion underneath a turbine rotor wheel, or a blade attachment.

In one embodiment, the revolutionary body 106 has a mass of greater than about 3 Tons, between about 3 Tons and about 150 Tons, between about 3 Tons and about 50 Tons, between about 50 Tons and about 100 Tons, between about 100 Tons and about 150 Tons, about 50 Tons, about 100 Tons, about 150 Tons, or any suitable combination, sub-combination, range, or sub-range therein. In one embodiment, features are machined into the shaft surface. The features form an area for the phased array devices 112 for positioning and/or securing.

The phased array devices 112 are configured for transmitting and/or receiving an ultrasonic phased array wave or beam 115. The phased array devices 112 are grouped into arrangements, each arrangement including a transmitting phased array device 120 and a receiving phased array device 130. In one embodiment, the transmitting phased array device 120 is positioned relative to the receiving phased array device 130 to generate a field through a predetermined volume of the revolutionary body 106. In one embodiment, the arrangement is situated on a periphery of the revolutionary body 106, and configured to transmit the ultrasonic phased array wave or beam 115 from the transmitting phased array device 120 to the receiving phased array device 130, thereby obtaining ultrasonic detection information relating to the revolutionary body 106.

In one embodiment, the positioning of the phased array devices 112 is adjusted to provide a desired degree of interrogation by the ultrasonic phased array wave or beam 115. In a further embodiment, the positioning of the phased array devices 112 is automated to provide the desired degree of interrogation by the ultrasonic phased array wave or beam 115. In one embodiment the phased array devices 112 are substantially planar. The phased array devices 112 have a plurality of sub-elements, the sub-elements being transducers (for example, 4 sub-elements, 8 sub-elements, 16 sub-elements, 32 sub-elements, 64 sub-elements, or 128 sub-elements), a predetermined operational frequency (for example, including, but not limited to, between about 1 MHz and about 10 MHz), or a combination thereof.

In one embodiment, the phased array wave or beam 115 travels through a region of the revolutionary body 106 to determine the presence or absence of a reflecting feature 114. In the absence of the reflecting feature 114 being within the path of the phased array wave or beam 115, the phase array wave or beam 115 is not reflected. In the presence of the reflecting feature being within the path of the phased array wave or beam 115, the phased array wave or beam 115 is reflected and/or refracted or otherwise modified. The reflecting feature 114 is a discontinuity within the revolutionary body 106, the discontinuity including, but not limited to, a void, a defect, a fatigued material, a crack, corrosion, another material difference, or a combination thereof. In the absence of the reflecting feature 114, the arrangement (including the transmitting phased array device 120 and the receiving phased array device 130) is moved incrementally along an axial length 104 of the revolutionary body 106 to detect a presence of the reflecting feature 114 in the revolutionary body 106. In another embodiment, the revolutionary body 106 is stationary and the arrangement is moved circumferentially about the revolutionary body 106. In one embodiment, the revolutionary body 106 is rotated axially about the centerline 110 at between about 1 and about 2 rotations per minute, between about 0.5 and about 1.5 rotations per minute, between about 0.5 and about 1 rotation per minute, between about 1 and about 1.5 rotations per minute, between about 1.5 and about 2 rotations per minute, or any suitable combination, sub-combination, range, or sub-range therein.

In one embodiment, the system 100 is used to validate and/or analyze the reflecting features 114 detected through the incremental movement of the arrangement (including the transmitting phased array device 120 and the receiving phased array device 130) and/or found by other methods, such as pulse echo. The system 100 is positioned relative to a location corresponding to the reflecting feature 114, and the phased array wave or beam 115 obtains ultrasonic detection information relating to the reflecting feature 114 within the revolutionary body 106. In one embodiment, the phased array wave or beam 115 from the transmitting phased array device 120 contacts the reflecting feature 114, the reflecting feature 114 distorting the phased array wave or beam 115. The phased array wave or beam 115 is distorted by parameters of the reflecting feature 114 such as, but not limited to, size, orientation relative to incident sound wave or beam, morphology, sound path travel, and suitable combinations thereof.

Analysis of the phased array wave or beam 115 received by the receiving phased array device 130 provides information about the presence and/or parameters of the reflecting feature 114. The information obtained characterizes a morphology of the reflecting feature 114, the morphology including, but not limited to, size, shape, orientation, geometric and material aspects, or a combination thereof. Repositioning of the phased array devices 112 on the periphery of the revolutionary body 106 obtains responses from various perspectives of the same reflecting feature 114. In one embodiment, the ultrasonic detection information relating to the reflecting feature 114 includes, but is not limited to, location, orientation, size, validity of the reflecting feature 114 detected, and combinations thereof.

The transmitting phased array device 120 and the receiving phased array device 130, in general, are positioned at an angle with respect to each other and/or the revolutionary body 106. The transmitting phased array device 120 emits the phased array wave or beam 115 at a predetermined transmission angle. In one embodiment, the predetermined transmission angle is adjustable. In one embodiment, the angles of the transmitting phased array device 120 and the receiving phased array device 130 differ. In one embodiment, the angles of the transmitting phased array device 120 and the receiving phased array device 130 are the same or substantially the same.

Suitable transmitting angles for the receiving phased array device 130 and/or the transmitting phased array device 120 include, but are not limited to, being arranged relative to a parallel of the centerline 110, between about 0 degrees and about 90 degrees, between about 1 degree and about 89 degrees, between about 0 degrees and about 80 degrees, between about 0 degrees and about 70 degrees, between about 10 degrees and about 80 degrees, between about 10 degrees and about 60 degrees, between about 45 degrees and about 80 degrees, between about 30 degrees and about 60 degrees, between about 30 degrees and about 45 degrees, between about 45 degrees and about 60 degrees, at about 10 degrees, at about 30 degrees, at about 45 degrees, at about 60 degrees, at about 80 degrees, or any suitable combination, sub-combination, range, or sub-range therein.

For example, referring to FIG. 1, the phased array devices 112 are situated in a first position 102. In the first position 102 the phased array wave or beam 115 exits the transmitting phased array device 120 at a first transmission angle 117 and reflects off of the reflecting feature 114, forming a first reflection angle 119. Referring to FIG. 2, the phased array devices 112 are situated in a second position 202. In the second position 202 the phased array wave or beam 115 exits the transmitting phased array device 120 at a second transmission angle 217 and reflects off the reflecting feature 114, forming a second reflection angle 219. In one embodiment, the first transmission angle 117 is the same as the second transmission angle 217, and forms the first reflection angle 119 different from the second reflection angle 219. In one embodiment, the first transmission angle 117 differs from the second transmission angle 217, and forms the first reflection angle 119 different from the second reflection angle 219.

In one embodiment, the phased array wave or beam 115 is skewed to obtain data from, but not limited to, an area not directly accessible by the phase array devices 112. Skewing the phased array wave or beam 115 includes rotating the phased array wave or beam 115 exiting the transmitting phased array device 120 about a surface normal.

In one embodiment, the system 100 includes a plurality of the arrangements (each of the arrangements includes the transmitting phased array device 120 and the receiving phased array device 130). The arrangements are situated in multiple positions on the revolutionary body 106, the receiving phased array devices 130 of the arrangements obtaining the ultrasonic detection information from different perspectives. The ultrasonic detection information from the arrangements is combined and analyzed with respect to various signal attributes, providing improved accuracy relating to the reflecting feature 114 within the revolutionary body 106.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An ultrasonic detection method, comprising the steps of:
   providing an ultrasonic detection system having a transmitting phased array device and a receiving phased array device;
   positioning the transmitting phased array device and the receiving phased array device in a pitch-catch manner on a periphery of a revolutionary body and at an angle with respect to each other and with respect to the revolutionary body; and
   interrogating the revolutionary body in the pitch-catch manner by transmitting a phased array wave through the revolutionary body from the transmitting phased array device thereby obtaining ultrasonic detection information about the revolutionary body, the receiving phased array device not receiving the phased array wave in the absence of a reflecting feature in the path of the transmitted phased array wave, and the receiving phased array device receiving a reflected, refracted or otherwise modified phased array wave when the reflecting feature is present in the path of the transmitted phased array wave.

2. The method of claim 1, wherein the revolutionary body is selected from the group consisting of items manufactured from a monolithic forging, a turbine rotor, a shaft of a solid steam rotor, a portion underneath a turbine rotor wheel, and a blade attachment.

3. The method of claim 1, wherein the transmitting phased array device and the receiving phased array device form an arrangement of phased array devices.

4. The method of claim 3, further comprising a plurality of arrangements of phased array devices.

5. The method of claim 4, wherein each arrangement of phased array devices obtains the ultrasonic detection information from a different position.

6. The method of claim 1, wherein the transmitting phased array device is positioned relative to the receiving phased array device to generate a field through a predetermined volume of the revolutionary body.

7. The method of claim 6, wherein the positioning of the transmitting and receiving phased array devices is automated.

8. The method of claim 1, further comprising analyzing the reflecting feature when the receiving phased array device receives the reflected, refracted or otherwise modified phased array wave.

9. The method of claim 1, wherein the reflecting feature comprises a flaw selected from the group consisting of a void, a defect, a fatigued material, a crack, and corrosion.

10. The method of claim 1, wherein the reflecting feature distorts the transmitted phased array wave.

11. The method of claim 10, wherein the transmitted phased array wave is distorted by parameters of the reflecting feature selected from the list consisting of size, orientation relative to incident sound wave, morphology, and sound path travel.

12. The method of claim 11, wherein each parameter distorts the transmitted phased array wave in an identifiable manner.

13. The method of claim 1, wherein the transmitting phased array device emits the phased array wave at a predetermined transmission angle.

14. The method of claim 13, further comprising adjusting the predetermined transmission angle.

15. The method of claim 1, further comprising skewing the transmitted phased array wave exiting the transmitting phased array device.

16. The method of claim 1, wherein the transmitting phased array device has a predetermined operational frequency.

17. The method of claim 1, wherein each of the transmitting and receiving phased array devices further comprises a plurality of transducers.

18. An ultrasonic detection method, comprising the steps of:
   providing an ultrasonic detection system having a transmitting phased array device and a receiving phased array device;
   positioning the transmitting phased array device and the receiving phased array device in a pitch-catch manner at an angle with respect to each other on a periphery of a turbine rotor;
   transmitting a phased array wave from the transmitting phased array device into the turbine rotor, the phased array wave not being received by the transmitting phased array device;
   adjusting the positioning of the transmitting phased array device or the receiving phased array device on the periphery of the turbine rotor; and
   transmitting the phased array wave from the transmitting phased array device into the turbine rotor, the phased array wave reflecting off of the reflecting feature and being received by the receiving phased array device in the pitch-catch manner after reflection off of the reflecting feature.

19. An ultrasonic analysis method, comprising the steps of:
   detecting a reflecting feature within a revolutionary body;
   providing an ultrasonic analysis system having a transmitting phased array device and a receiving phased array device; and
   validating the detected reflecting feature with the ultrasonic analysis system utilizing the steps of:
      positioning the transmitting phased array device and the receiving phased array device in a pitch-catch manner in a predetermined configuration on a periphery of the revolutionary body around the detected reflecting feature;

transmitting phased array waves from the transmitting phased array device into the revolutionary body;

reflecting the phased array waves off of the detected reflecting feature within the revolutionary body; and receiving the phased array waves at the receiving phased array device in the pitch-catch manner, thereby obtaining ultrasonic information about the reflecting feature selected from the group consisting of size, orientation relative to an incident sound wave, morphology, sound path travel, and combinations thereof.

20. The ultrasonic analysis method of claim 19 wherein at least one of the transmitting phased array device and the receiving phased array device further includes a plurality of phased array devices.

* * * * *